US00PP24683P3

(12) United States Plant Patent
Khemakongkanond

(10) Patent No.: US PP24,683 P3
(45) Date of Patent: Jul. 22, 2014

(54) *DRACAENA* PLANT NAMED 'KKDR201203'

(50) Latin Name: *Dracaena reflexa*
Varietal Denomination: KKDR201203

(71) Applicant: Kanachana Khemakongkanond, Bangkok (TH)

(72) Inventor: Kanachana Khemakongkanond, Bangkok (TH)

( * ) Notice: Subject to any disclaimer, the term of this patent is extended or adjusted under 35 U.S.C. 154(b) by 36 days.

(21) Appl. No.: 13/694,421

(22) Filed: Nov. 29, 2012

(65) Prior Publication Data

US 2014/0150152 P1 May 29, 2014

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Kent L Bell
(74) *Attorney, Agent, or Firm* — Cassandra Bright

(57) ABSTRACT

A new and distinct *Dracaena* cultivar named 'KKDR201203' is disclosed, characterized by distinctive foliage variegation pattern unlike other known *Dracaena reflexa* cultivars, as well as long narrow leaves. The new variety is a *Dracaena*, typically produced as an indoor ornamental plant.

1 Drawing Sheet

Latin name of the genus and species: *Dracaena reflexa*.
Variety denomination: 'KKDR201203'.

BACKGROUND OF THE INVENTION

The new cultivar is the product of chance discovery. The new variety originated as a naturally occurring mutation, whole plant of an unpatented unnamed variety of *Dracaena reflexa*.

The new variety was first discovered by the inventor, Kanchana Khemakongkanond, a citizen of Thailand, in August of 2004, in a nursery in Bangkok, Thailand. After identifying the new variety as a potentially interesting selection, the inventor continued confidential testing and propagation of 'KKDR201203', assessing stability of the unique characteristics of this variety.

Asexual reproduction of the new cultivar 'KKDR201203' by vegetative cuttings was first performed at the same nursery in Bangkok, Thailand during November of 2004. Subsequently at least three generations have been produced from vegetative cuttings, and have shown that the unique features of this cultivar are stable and reproduced true to type.

SUMMARY OF THE INVENTION

The cultivar 'KKDR201203' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KKDR201203'. These characteristics in combination distinguish 'KKDR201203' as a new and distinct *Dracaena* cultivar:

1. Distinctive foliage variegation pattern unlike other known *Dracaena reflexa* cultivars.
2. Very narrow, long narrow leaves.

PARENT COMPARISON

Plants of the new cultivar 'KKDR201203' are similar to the unnamed unpatented parent, in most horticultural characteristics. The new variety, however, produces variegated leaves, whereas the parent produces green leaves.

COMMERCIAL COMPARISON

Plants of the new cultivar 'KKDR201203' are comparable to the variety *Dracaena* 'Anita' unpatented. The two *Dracaena* varieties are similar in most horticultural characteristics, including plant habit, and having long, narrow foliage. However, the new variety 'KKDR201203' differs in having variegated leaves, whereas 'Anita' produces green leaves.

BRIEF DESCRIPTION OF THE PHOTOGRAPH

The accompanying photograph in FIG. 1 illustrates in full color a typical plant of 'KKDR201203' grown in a commercial greenhouse in Honselersdijk, the Netherlands. This plant is approximately 6 months old, shown planted in a 12 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'KKDR201203' plants grown according to the following protocols.

Plants were grown in Honselersdijk, the Netherlands, under greenhouse conditions, with temperatures ranging approximately from 25° C. to 36° C. during the day and 17° C.

to 25° C. at night with natural sunlight. Measurements and numerical values below represent averages of typical plant types.

Botanical classification: *Dracaena reflexa* 'KKDR201203'.

PROPAGATION

Propagation details:

Time to initiate rooting: About 6 weeks at approximately 25° C. to 28'C.

Root description: Moderately thick, moderately fibrous, not fleshy, young roots cream-white, older roots Greyed-Orange 163D.

PLANT

Age of plant described: 6 months

Pot size of plant described: 17 cm circular pot.

Growth habit: Upright.

Height: Approximately 37.5 cm.

Plant spread: Approximately 42.5 cm.

Growth rate: Moderate, approximately 10 cm per month.

Branching characteristics: Not free branching, typically growing with one main stem from the base. Will only develop lateral branches after pinching/pruning.

Diameter of stem: Approximately 0.6 cm.

Internode length: Average 0.4 cm.

Texture of stem: Smooth, dull.

Color of stem: Green; near RHS 137C.

Stem strength: Very strong.

Number of leaves per stem: Average 50.

FOLIAGE

Leaf:

*Arrangement*.—Alternate (spirally). Average Length: Approximately 23.6 cm. Average Width: Approximately 1.2 cm. Shape of blade: Lorate. Aspect: Leaves in an average angle of 50° to main stem (=0°), tips curved downward in an average angle of 40° to horizontal)(=0°). Apex: Narrow acuminate. Base: Broad cuneate. Attachment: Sheathing. Margin: Entire. Texture of top surface: Smooth, moderately glossy. Texture of bottom surface: Smooth, moderately glossy.

*Color*.—Young foliage upper side: Green; near RHS N137A, broadly margined and irregular striped (axial) Yellow-green; near RHS 145C and 150D, both colors present. Young foliage under side: Green; near RHS N137B, broadly margined and irregular striped (axial) Yellow-green; near RHS 138A and 154D, both colors present. Mature foliage upper side: Green to yellow-green; in between near RHS N137A and 147A, both colors present, narrowly margined and irregular striped (axial) Greyed-green; near RHS 190C to 191D. Mature foliage under side: Green; near RHS 137B, broadly margined and irregular striped (axial) lighter; near RHS 138B and 138C, both colors present.

*Venation*.—Type: Parallel. Color: Upperside: As leaf blade. Underside: As leaf blade.

*Sheath*.—Average Length: Approximately 0.3 cm. Average Width: Approximately 0.8 cm. Color: Green; near RHS 143A. Texture: Smooth, slightly glossy. Other Distinguishing Characteristics: No.

FLOWERING CHARACTERISTICS

Flowering not observed to date.

REPRODUCTIVE ORGANS

Not observed to date.

OTHER CHARACTERISTICS

Disease resistance: Good resistance to the normal diseases found in *Dracaena*.

Drought tolerance and cold tolerance: Normal for species, USDA zone 10 and higher.

Fruit/seed production: No fruits/seeds detected to date.

What is claimed is:

1. A new and distinct cultivar of *Dracaena* plant named 'KKDR201203' as herein illustrated and described.

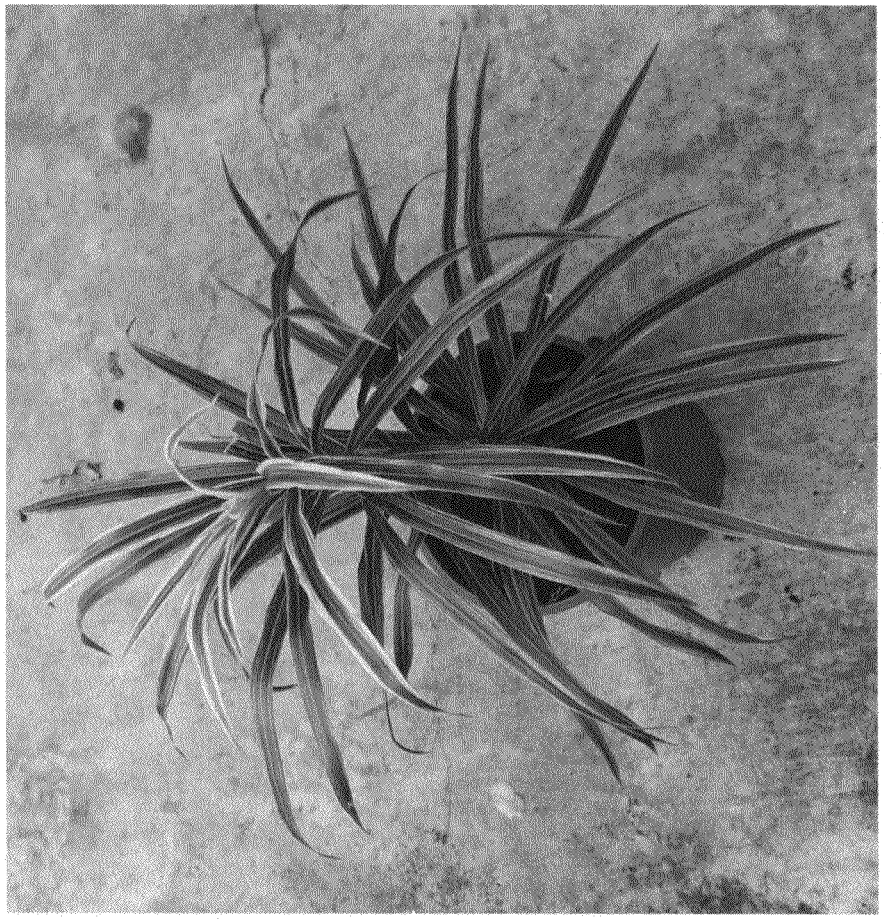

* * * * *